United States Patent [19]

Pederson et al.

[11] Patent Number: 5,311,358
[45] Date of Patent: May 10, 1994

[54] UNIVERSAL MICROSCOPE DRAPE

[75] Inventors: Jane M. Pederson; William R. Johnson, both of Largo, Fla.

[73] Assignee: Time Surgical, Inc., Largo, Fla.

[21] Appl. No.: 958,497

[22] Filed: Oct. 8, 1992

[51] Int. Cl.$^5$ .................. G03B 11/04; B65D 85/38
[52] U.S. Cl. ..................... 359/510; 359/511; 206/316.1
[58] Field of Search ............... 359/503–504, 359/506, 507, 510–514, 600, 611, 612, 808–812; 206/305, 316.1, 316.3

[56] References Cited

U.S. PATENT DOCUMENTS

| 3,133,140 | 5/1964 | Winchell | 359/511 |
| 3,528,720 | 9/1970 | Treace | 206/316.1 |
| 3,698,791 | 10/1972 | Walchle et al. | 359/510 |
| 3,796,477 | 3/1974 | Geraci | 359/511 |
| 4,266,663 | 5/1981 | Geraci | 359/510 |
| 4,561,540 | 12/1985 | Hunter et al. | 206/305 |
| 4,799,779 | 1/1989 | Mesmer | 359/510 |
| 4,807,594 | 2/1989 | Chatenever | 359/513 |
| 5,050,963 | 9/1991 | Murakami | 359/808 |

Primary Examiner—Loha Ben
Assistant Examiner—Thong Nguyen
Attorney, Agent, or Firm—Herbert W. Larson

[57] ABSTRACT

A universal inner diameter mounting ring contains an annular groove within its inner circumference, the ring being integral with a microscope drape. A microscope adapter housing having a universal outer diameter with a protruding annular ring around its circumference engages the groove on the mounting ring. The adapter engages the inner mounting threads of a microscope body at a first end and the threads of an objective lens housing at a second end.

7 Claims, 3 Drawing Sheets

UNIVERSAL MICROSCOPE DRAPE

BACKGROUND OF THE INVENTION

1. Field of the Invention

This application relates to microscope drapes. More particularly, it refers to an operating room microscope objective lens adapter with a fixed outer diameter and shaped circumference engaging a cooperating snap on ring integral with a microscope drape.

2. Description of the Prior Art

Operating room microscope drapes are in common usage on microscopes in many surgical procedures to insure that the operating area is free from contamination caused by the microscope or its support arm. A single mounting ring housing enclosing a plastic lens is integral with the drape. The mounting ring housing is usually friction fitted to the outer diameter of the microscope objective lens housing. Problems with this procedure have arisen for two reasons. First, the outer diameter and thickness of the objective lens housing differs depending on the manufacture and style of the microscope and its corresponding lens. This requires an inventory of several different drapes containing mounting rings of varying diameters and depths to accommodate the different microscope objective lens housings. This multiple inventory requirement can be quite confusing in the operating room. As an example, it is estimated that at least 70% of all U.S. hospitals have multiple brands of operating room microscopes currently in use. Pulling the incorrect drape for a procedure could result in a serious delay during microsurgery. Secondly, several surgical microscopes have objective lens housings which are quite close in diameter. If the incorrect drape is pulled and the friction fit is not perfect, sudden slippage of the mounting ring into the surgical field could occur during an operation which could result in serious complications to the patient. A universal mounting ring is needed that can be fitted to all operating room microscopes without any fear of slippage.

SUMMARY OF THE INVENTION

I have designed a novel universal mounting ring integral with a microscope drape that will mount on the exterior circumference of an adapter housing fitted to the objective lens housing of a microscope. Different adapters will fit each different manufacture and style of microscope but each will have the same outside diameter and circumference to accommodate a snap on fit with the inner circumference of the drape mounting ring housing. As a result, only one style of drape need be maintained in inventory by a hospital.

My mounting ring will have an inside diameter of about 7 cm with an annular groove around the inner circumference. This groove receives a protruding annular member around the outside diameter of an adapter ring housing mounted at a first end to an inside surface of a microscope body. The microscope objective lens housing is mounted within a second end of the adapter ring. The first and second ends of the adapter ring will vary in each adapter to accommodate the exact mounting requirements of each microscope and objective lens housing, but the outside diameter and protruding annular member on the outside circumference will be identical in each adapter ring housing.

BRIEF DESCRIPTION OF THE DRAWINGS

The invention may be best understood by those having ordinary skill in the art by reference to the following detailed description when considered in conjunction with the accompanying drawings in which.

DETAILED DESCRIPTION OF THE INVENTION

Figure 1:
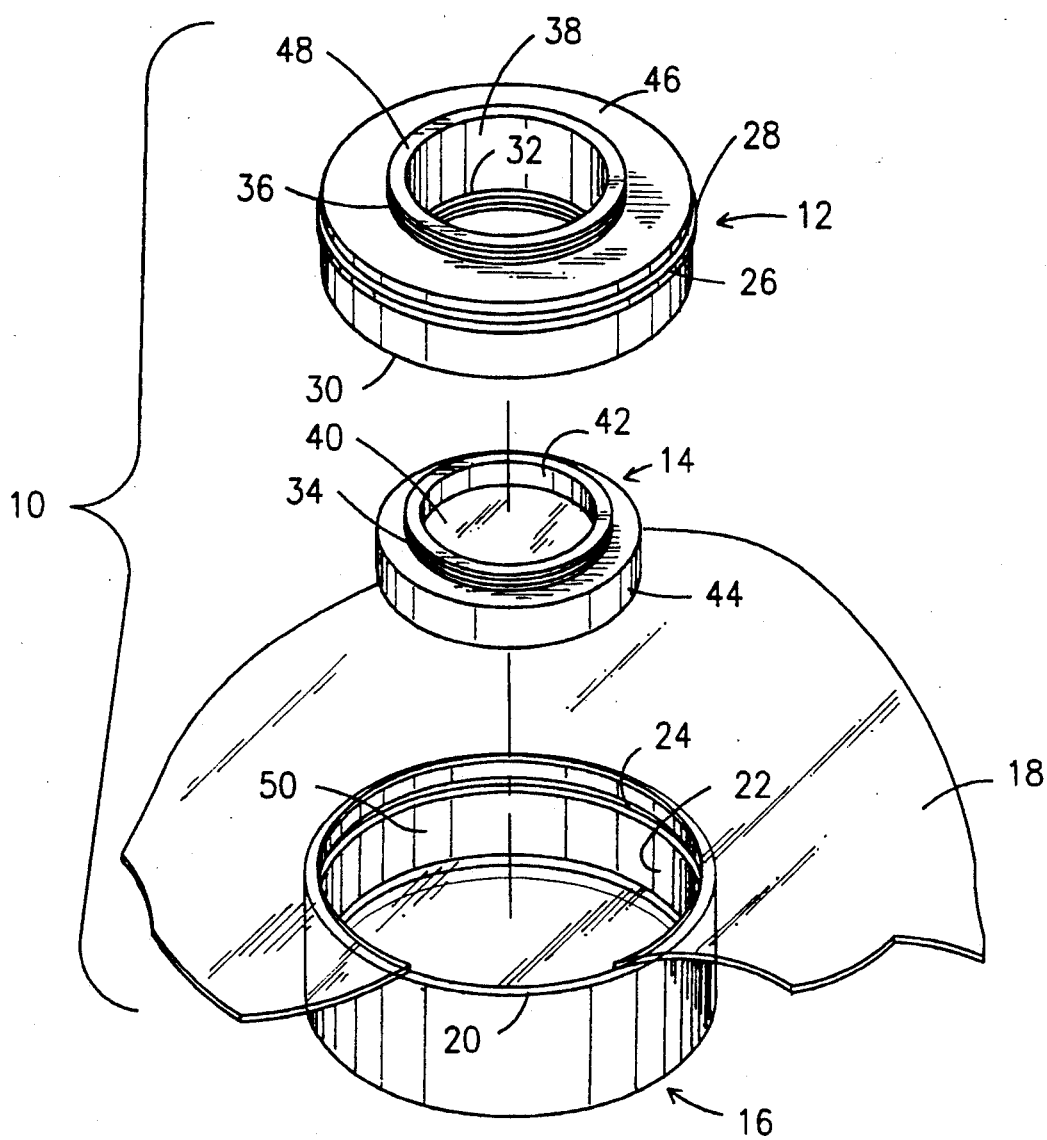
FIG. 1 is an exploded view of the mounting ring and drape, together with the microscope objective lens housing and adapter ring housing.

Throughout the following detailed description, the same reference numerals refer to the same elements in all figures.

The universal microscope drape assembly 10 has an adapter ring housing 12, a microscope objective lens housing 14, a mounting ring housing 16, and a thin polymer sheet forming a drape 18 as shown in FIG. 1.

The mounting ring housing 16 is integral with drape 18 by a seal along edge 20. The inside circumference 22 of the mounting ring housing 16 contains a groove 24 which is annular in shape to accommodate a protruding ring 26 from the adapter ring housing 12 as shown in FIG. 1. The inner circumference wall 22 of the mounting ring and the outer circumference wall 28 of the adapter ring provide a close airtight fit after the protruding ring 26 is locked in place in receiving groove 24. The microscope objective lens housing 14 is mounted within the second end 30 of the adapter ring housing 12 and threads 32 within adapter ring housing 12 engage threads 34 on an outer circumference of the microscope objective lens housing 14. Threads 36 on an outer circumference of the adapter ring housing 12 accommodate to a set of threads within the microscope body inner circumference (not shown). Threads 36 and 32 will vary on each adapter 12 so that there is an exact fit with a particular manufacture or style of microscope to which the adapter is fitted. The outer circumference 28 and protruding ring 26 will be the same diameter on each adapter ring so that they will accommodate the mounting ring housing 16.

Figure 2:
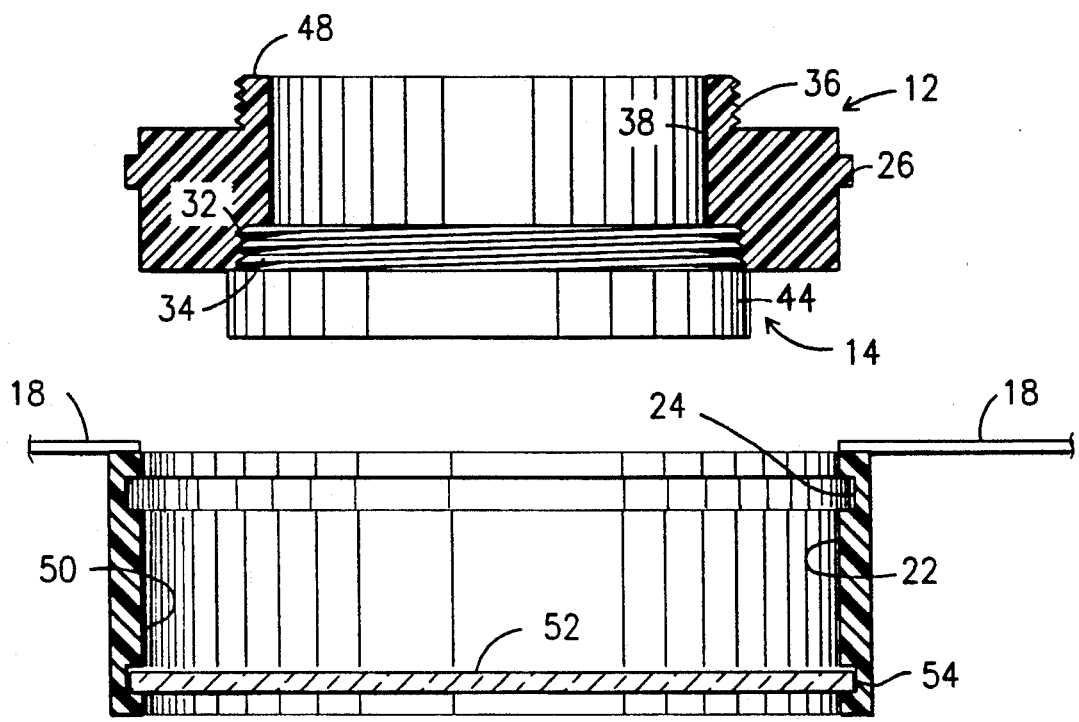
FIG. 2 is a sectional elevational view of the adapter ring housing and microscope objective lens housing before snapping into the mounting ring housing.
Figure 3:
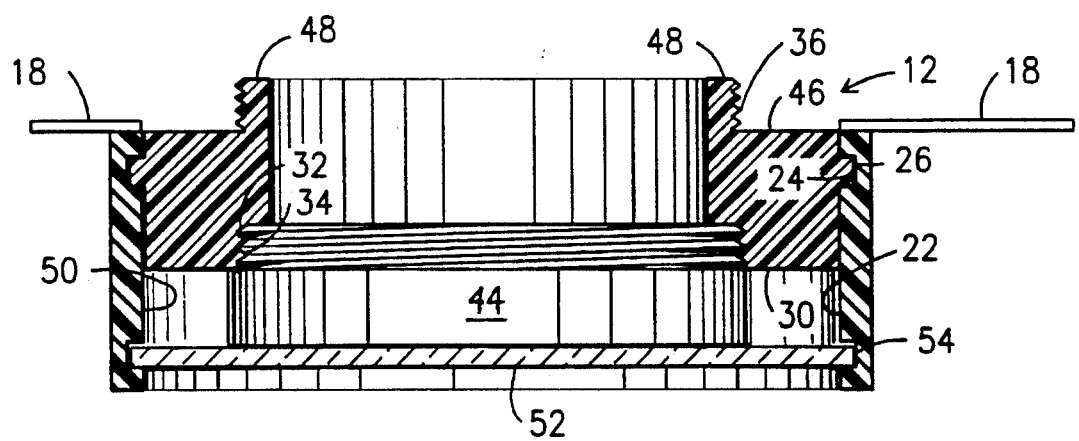
FIG. 3 is a sectional elevational view of the adapter ring housing and microscope objective lens housing mounted within the mounting ring housing.

Referring to FIG. 2, the adapter ring housing 12 with threads 32 on its inner wall diameter 38 receives the outer threads 34 from a microscope objective lens housing 14. A microscope lens 40 is integral with the interior wall 42 of the microscope objective lens housing 14. A bottom portion or skirt 44 of the objective lens housing 14 is received within mounting ring housing inner circumference 22 and abuts on the plastic lens 52. Skirt 44 is below the adapter 12 when engaged to the adapter as seen in FIGS. 2 and 3 to a depth of about 1-5 centimeters.

The adapter ring housing 12 has an upper flange 46 fitting flush against and upper annular member or first end 48 for insertion within, the microscope body.

Figure 4:
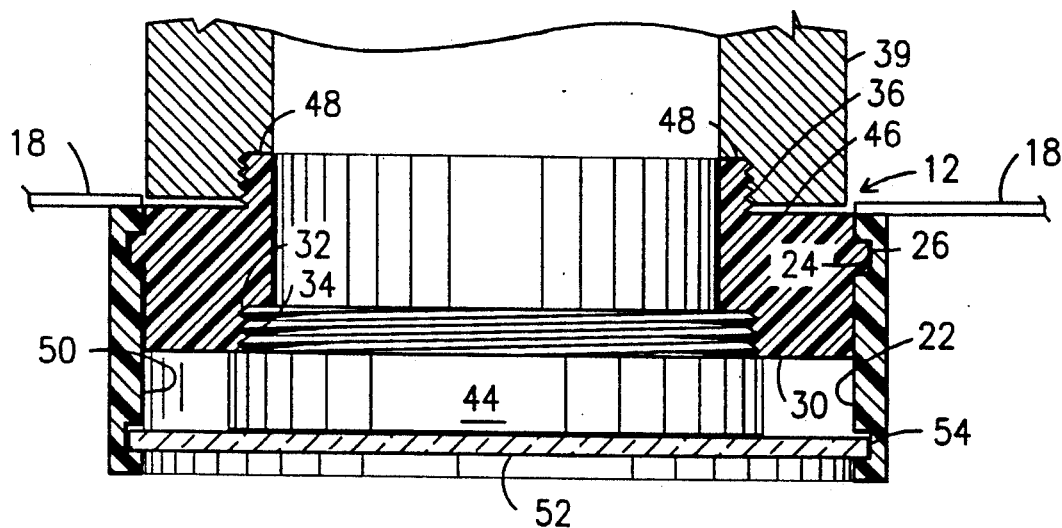
FIG. 4 is a sectional elevational view of the adapter ring housing threads attached to threads of a microscope housing.
Figure 5:
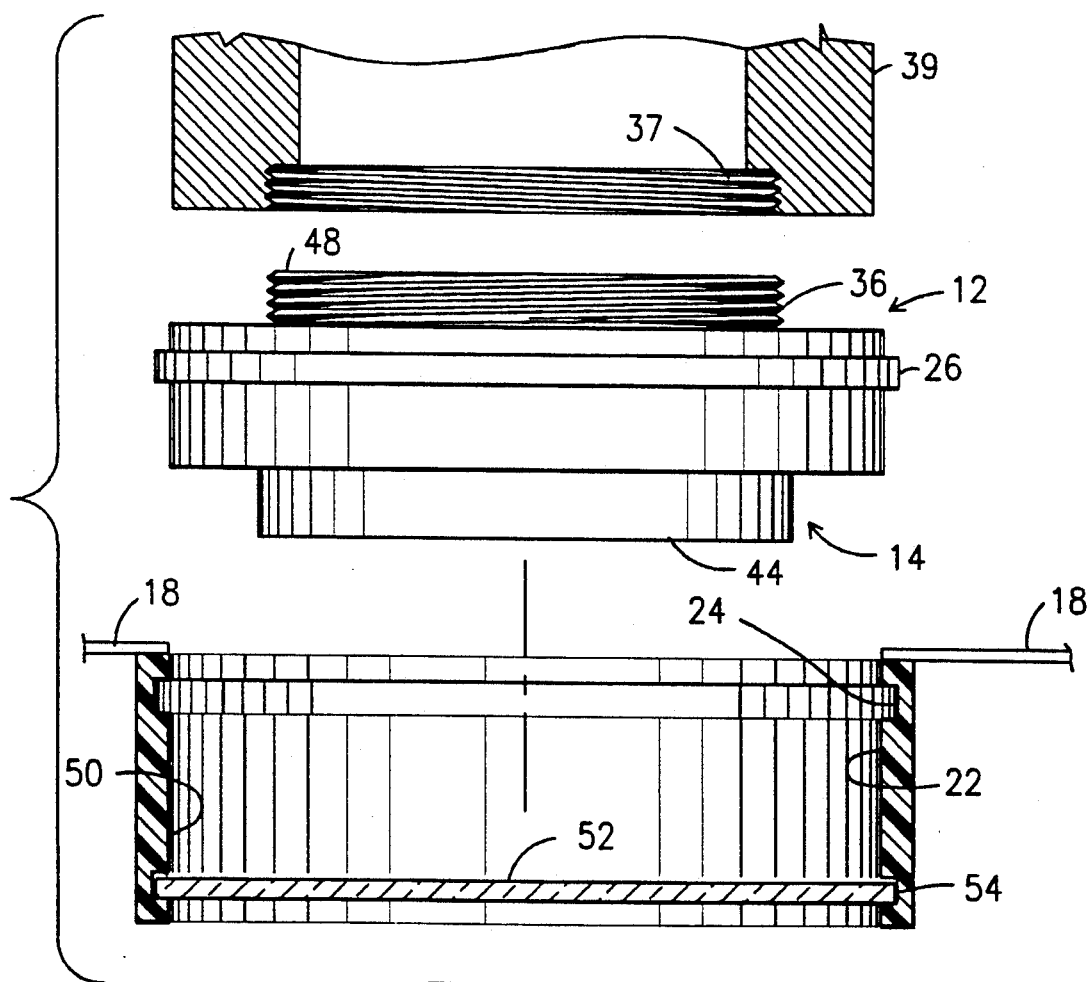
FIG. 5 is an exploded elevational view of the adapter ring housing threads configured to be screwed to threads of a microscope housing.

Threads 36 on the adapter ring housing 12 engage the corresponding threads 37 within the microscope 39 as shown in FIGS. 4 and 5. As shown in FIG. 3, the microscope objective lens housing 14 and adapter ring housing 12 are engaged by the respective threads 34 and 32. The adapter ring housing 12 with objective lens housing 14 engaged receives the mounting ring housing 16 by an upwards pushing of the mounting ring housing 16. The depth of the inner wall 50 of the mounting ring housing is sufficient to accommodate the outer diameter ring or skirt 44 of the microscope objective lens housing 14 so that the microscope objective lens housing 14 closely abuts the plastic lens 52 mounted within groove 54 of the mounting ring housing 16.

The mounting ring 16 can be made of a high strength plastic substance. The adapter ring housing 12 can be manufactured from an aluminum alloy or a high strength plastic such as DELRIN®, made by E. I. duPont de Nemours & Company, Inc.

Typical threads found in various commonly used microscopes have a range of 50 to 68 threads per millimeter in Storz, St. Louis, Topcon, Moeller Wedel and Jed-Med microscopes. In Zeiss OPMI 99, Zeiss MD, Cabot, Olympus, Elmed, Inami, AusJena, and Nikon microscopes there are 36 to 63 threads per 0.75 millimeters. Codman, OMS300 & 320 and Weck microscopes use the English system of thread sizes.

Substitution of other holding means for the groove 24 and protruding member 26 can be employed to confirm a secure mounting bond between the adapter ring housing and the mounting ring housing. The microscope drape 18 can be any type thin polymer sheet as shown on U.S. Pat. No. 4,561,540 and 3,528,720 which are herein incorporated by reference.

Having this described the invention, what is claimed and desired to be secured by Letters Patent is:

1. In a disposable thin polymer microscope drape assembly for maintaining a sterile envelope around an operating room microscope having a mounting ring housing integral with a drape for engagement with an objective lens housing of a microscope, the improvement comprising:
    an inner diameter of the mounting ring housing corresponding to an outside diameter of an adapter ring housing;
    a means for attaching the mounting ring housing to the adapter ring housing;
    a first end of the adapter ring housing having a means for engaging a microscope body;
    a second end of the adapter ring housing having a means for engaging a microscope objective lens housing; and
    the mounting ring housing having a depth to enclose a lower end of the microscope objective lens housing and retain a clear plastic lens.

2. The microscope drape assembly according to claim 1 wherein the means for attaching the mounting ring housing to the adapter ring housing is an annular groove within an interior wall of the mounting ring housing, the interior wall groove receiving an annular protrusion on an outer wall of the adapter ring housing when the mounting ring is pushed onto the adapter ring.

3. The microscope drape assembly according to claim 1 wherein the first end of the adapter ring housing has threads for engaging corresponding threads within the microscope body to provide the means for engaging the microscope body.

4. The microscope drape assembly according to claim 1 wherein the second end of the adapter ring housing has threads for engaging corresponding threads on a microscope objective lens housing.

5. The microscope drape assembly according to claim 1 wherein the adapter ring and mounting ring are made from a polymer.

6. The microscope drape assembly according to claim 4 herein the objective lens housing has a skirt descending about 1-5 centimeters below the adapter housing when the objective lens housing is threaded to the adapter housing.

7. In a disposable microscope drape assembly for maintaining a sterile envelope around an operating room microscope having a mounting ring housing integral with a drape for engagement an objective lens housing of a microscope, the improvement comprising:
    an inner wall diameter of the mounting ring housing corresponding to an outside wall diameter of an adapter ring housing;
    a first end of the adapter ring having threads compatibly engaged to threads within a body of the microscope;
    a second end of the adapter ring housing having threads compatibly engaged to threads in a top end of a microscope objective lens housing, the objective lens housing having a descending annular skirt at a bottom end; and
    the mounting ring having a depth sufficient to enclose the microscope objective lens housing skirt and having an annular groove on the inner wall to receive an annular protruding member on the outer wall of the adapter ring housing so that the assembly is locked in place over the microscope but can be disassembled for disposal of the mounting ring and drape.

* * * * *